United States Patent [19]

Schlaeppi et al.

[11] Patent Number: 5,576,188
[45] Date of Patent: Nov. 19, 1996

[54] IMMUNOLOGICAL DETECTION OF METOLACHLOR

[75] Inventors: Jean-Marc Schlaeppi, Basel; Klaus Ramsteiner, Hofstetten; Hans Moser, Magden, all of Switzerland

[73] Assignee: Ciba-Geigy Corporation, Tarrytown, N.Y.

[21] Appl. No.: 359,689

[22] Filed: Dec. 20, 1994

Related U.S. Application Data

[63] Continuation of Ser. No. 35,872, Mar. 23, 1994, abandoned, which is a continuation of Ser. No. 665,397, Mar. 6, 1991, abandoned.

[30] Foreign Application Priority Data

Mar. 9, 1990 [CH] Switzerland ............................. 762/90
Nov. 23, 1990 [CH] Switzerland ............................ 3378/90

[51] Int. Cl.$^6$ ..................... G01N 33/577; C12P 21/08; C07K 16/44
[52] U.S. Cl. .................. 435/7.93; 435/7.95; 435/172.2; 435/240.27; 436/548; 436/815; 530/388.9; 530/807
[58] Field of Search ................................ 435/7.93, 7.95, 435/240.27, 172.2; 436/531, 536, 528, 542, 548, 815; 530/388.9

[56] References Cited

FOREIGN PATENT DOCUMENTS 0340198  11/1989  European Pat. Off. .

OTHER PUBLICATIONS

Vanderlaan et al., Environ. Sci. Technol., vol. 22, pp. 247–254 (1988).
Schlaeppi et al., J. Agric. Food Chem., 37:1532–1538 (1989).
Wilson et al., Abstract 90–82263.
Fleeker, J. Assoc. Off. Anal. Chem., 70:874–878 (1987).
Kelly et al., J. Agric. Food Chem., 33:962–965 (1985).
Wie et al., J. Agric. Food Chem., 30:949–957 (1982).
Newsome, J. Agric. Food Chem., 33:528–530 (1985).
Feng et al., J. Agric. Food Chem., 38:159–163 (1990).
Ercegovich et al., J. Agric. Food Chem., 29:559–563 (1981).
E. Sevier et al., Clinical Chemistry, vol. 27, No. 11, pp. 1797–1806 (1981).

*Primary Examiner*—Mary E. Ceperley
*Attorney, Agent, or Firm*—Edward McC. Roberts; William A. Teoli, Jr.

[57] ABSTRACT

The present invention relates to monoclonal antibodies which are distinguished by high selectivity and affinity for metolachlor and which are therefore outstandingly suitable for use in an immunoassay for the rapid and efficient detection of metolachlor. Another aspect of the present invention relates to hybridoma cell lines which produce said monoclonal antibodies and to immunological methods for detecting metolachlor in samples of soil, water or air using said monoclonal antibodies and to the test kits which can be used within the scope of these detection methods.

43 Claims, No Drawings

IMMUNOLOGICAL DETECTION OF METOLACHLOR

This is a continuation of Ser. No. 08/035,872, filed Mar. 23, 1994, now abandoned, which is a continuation of Ser. No. 07/665,397, filed Mar. 6, 1991, now abandoned.

The present invention relates to monoclonal antibodies which are distinguished by high selectivity and affinity for metolachlor and which are therefore outstandingly suitable for use in an immunoassay for the rapid and efficient detection of metolachlor.

Another aspect of the present invention relates to hybridoma cell lines which produce said monoclonal antibodies and to immunological methods for detecting metolachlor using said monoclonal antibodies and to the test kits which can be used within the scope of these detection methods.

The use of synthetic herbicides for plant protection purposes and the environmental pollution associated therewith have recently become the focus of public discussion increasingly frequently.

Metolachlor is a widely used herbicide which is employed for plant protection purposes, especially for the selective control of various wild grasses in maize, cotton, potato, sorghum and sugar beet crops.

From the chemical viewpoint, metolachlor is 2-chloro-6'-ethyl-N-(2-methoxy-1-methyl-ethyl)acet-O-toluidide [see: The Pesticide Manual, 8th Edition, ed. by C. R. Worthing and S. B. Walker, The British Crop Protection Council, Thornton Heath CR4 7QB, UK, 1987, pages 568 and 569].

Metolachlor is currently detected in samples of soil and water primarily by gas or liquid chromatography (for example HPLC) [Hargrave HS and Merkle MG (1971); van Rensburg E (1985)].

However, all the said methods for detecting synthetic herbicides are associated with numerous disadvantages. Thus, for example, to determine metolachlor in samples of soil by GC or HPLC it is necessary to interpolate elaborate purification and concentration steps before the actual chromatographic analysis is carried out.

Other disadvantages of these methods may be regarded as being that, for example, element-specific detectors are employed in gas chromatography, while photometric detectors which are relatively non-specific are used in HPLC. With the exception of mass-spectroscopic detection, the basis for the chromatographic analyses is the determination of retention times for the particular substance. However, these values are relative and thus not structure-specific.

In order to avoid these previously described disadvantages of the established analytical methods, there have been recent attempts to develop immunological methods for the agricultural sector in addition to those already routinely employed in clinical diagnosis for detecting a wide variety of antigens, especially for the quantitative and qualitative determination of agricultural chemicals in samples of soil, water or air.

Thus, for example, a start has now been made on the development of immunological methods for the detection of certain herbicides such as 2,4-dichlorophenoxyacetic acid (Fleeker, 1986) or chlorsulfuron (Kelley et al, 1985) as well as various pesticides such as diflubenzuron (Wie and Hammock, 1982), metalaxyl (Newsome, 1985), alachlor (Feng et al, 1990) or parathion (Ercegovich et al, 1981). A method has already been described (U.S. Pat. No. 4,530,786) for the immunological detection of atrazine too, but this is based, as are the previously mentioned methods, on the use of polyclonal antisera obtained from animals which have previously been immunised with an appropriate antigen.

Polyclonal antisera have a very heterogeneous composition, that is to say they contain a large number of different antibodies which react with different epitopes on the particular antigen. This heterogeneous composition of polyclonal antisera comes about because, when an experimental animal is immunised with a particular antigen, there is always simultaneous stimulation of several antibody-producing cell clones, each of which recognises a different epitope on the antigen molecule and therefore different antibodies are produced by the stimulated cell clones.

This is the reason why sera from immunised animals are always polyclonal and thus heterogeneous with respect both to their specificity and to their membership of the individual classes of immunoglobulins.

This heterogeneity in the composition of polyclonal antisera can thus lead to compounds which are closely related structurally, such as, for example, metolachlor and alachlor, being impossible to differentiate to a sufficient extent when polyclonal antibodies are used in an immunoassay. In order to overcome these disadvantages of polyclonal antisera, increased efforts have recently been made to develop monoclonal antibodies for the agricultural sector too. Thus, Schlaeppi et al (1989) report the preparation and use of monoclonal antibodies against atrazine and hydroxyatrazine in an enzyme-coupled immunoassay. By contrast, the preparation of monoclonal antibodies against metolachlor which have a sufficiently high affinity for the target substance and are thus suitable for use according to the invention in one of the known immunoassays has not yet succeeded.

Hence the object which this invention was intended to achieve was primarily to provide an immunoassay which is simple to manipulate, efficient and highly selective for rapid and reliable detection of metolachlor in samples of soil, water and air and in extracts of biological material.

It has now been possible, surprisingly, to achieve this object by the present invention, specifically by providing monoclonal antibodies with high specificity and affinity for metolachlor by using the hybridoma/monoclonal antibody technology known per se.

The use of hybrid somatic cell lines (hybridomas) as source of antibodies against very particular antigens derives from the work of Köhler and Milstein (Nature, 256: 495–97, 1975).

The antibodies which can be obtained by the process described therein differ very greatly from those obtained from antisera of conventionally immunised animals.

The principle of the hybridoma/monoclonal antibody technology is based on the observation that the hybrid cell resulting from the fusion of two somatic cells has characteristic features of both parent types.

In the case of monoclonal antibody production, the ability to synthesise the specific antibody derives from an immunocompetent B cell (usually a spleen cell) which has been taken from a previously immunised donor animal, while the ability for the cells to divide continuously in culture is contributed by the other fusion partner, a tumour cell line (often a myeloma).

Each of these hybrid cell lines synthesises a homogeneous immunoglobulin which represents only a single representative of the large number of possible antibodies which can be synthesised in vivo by an animal in response to an antigen.

Because each immunoglobulin-producing clone is characterised by a single type of antibodies, the term monoclonal antibodies is generally used.

The advantages of monoclonal versus polyclonal antibodies are numerous:

a) monoclonal antibodies can be obtained in large number and in high purity, b) the preparation of monoclonal antibodies is homogeneous with respect to antigen reactivity and does not change over the course of time either, c) hybridomas producing monoclonal antibodies can be stored for years and decades without losing their specific properties, i.e. the production of specific monoclonal antibodies, thereby, d) monoclonal antibodies are more suitable for use as standard reagents than are polyclonal antisera, because the latter are adversely affected by a wide range of variation in respect of, for example, α) the taking of blood from immunised animals for obtaining the antiserum, β) a constant availability of material for additional immunisations, γ) the limited lifespan of the donor animals.

Monoclonal antibodies, which have now been prepared against a large number of antigens, are well established primarily in medical diagnosis and can no longer be dispensed with therefrom.

The present invention has now succeeded for the first time, by using the hybridoma/monoclonal antibody technology which is known per se and has been briefly described previously, in providing monoclonal antibodies which have high specificity and affinity for the herbicide metolachlor and which, by reason of their high specificity and, resulting therefrom, the low cross-reactivity with structurally related compounds, are outstandingly suitable for use in an immunoassay for the rapid and reliable detection of metolachlor and thus can also be used for differentiation of metolachlor from structurally related compounds or inactive metabolites.

The present invention primarily relates to monoclonal antibodies and derivatives thereof which have high specificity and affinity for metolachlor and which show essentially no cross-reactivity with the best known metolachlor analogues, but especially no cross-reactivity with the metolachlor analogue alachlor.

Particularly preferred within the scope of the present invention are monoclonal antibodies and derivatives thereof which have a high specificity and affinity for metolachlor and which show a cross-reactivity with the best known structurally related compounds which is below 10%, but particularly below 2% and very particularly preferably below 0.1%.

By derivatives of monoclonal antibodies are meant within the scope of the present invention, for example, antibody fragments which still have high specificity and affinity for the antigenic determinants of metolachlor, furthermore radioactively labelled monoclonal antibodies which are labelled, for example, with radioactive iodine ($^{125}$I, $^{131}$I), carbon ($^{14}$C), sulfur ($^{35}$S), tritium ($^{3}$H) or the like, conjugates of monoclonal antibodies with biotin or avidin, with enzymes such as horseradish peroxidase, alkaline phosphatase, β-D-galactosidase, glucose oxidase, glucoamylase, carbonic anhydrase, acetylcholinesterase, lysozyme, malate dehydrogenase or glucose-6-phosphate dehydrogenase, furthermore conjugates of monoclonal antibodies with bioluminescent (for example luciferase), chemoluminescent (for example acridinium esters) or fluorescent (for example phycobiliproteins) agents. Likewise embraced by the present application are bispecific and so-called cross-linked antibodies. This list of examples of possible antibody derivatives merely serves to illustrate the present invention and is not intended to limit the subject-matter of the invention in any way.

The term "essentially no cross-reactivity" is intended to mean within the scope of this invention that the monoclonal antibodies specific for metolachlor have a reactivity with non-specific epitopes of other compounds, especially structurally related compounds, of less than 10%, but preferably of less than 2% and very particularly preferably of less than 0.1%.

The percentage cross-reactivity is to be defined within the scope of this invention by the following relation:

(Metolachlor concentration for 50% inhibition/concentration of the metolachlor analogues for 50% inhibition)×100.

A 50% inhibition can be determined, for example, with the aid of a competitive ELISA assay (compare Example 8). This then corresponds, for example, to that antigen concentration which leads to 50% inhibition of antibody binding to the carrier-bound antigen.

The present invention also relates to hybridoma cell lines which synthesise and, preferably, secrete into the surrounding medium the monoclonal antibodies previously characterised in detail.

The present invention particularly relates to a hybridoma cell line which produces a monoclonal antibody which has high specificity and affinity for metolachlor and shows essentially no cross-reactivity with the best known structurally related compounds, but especially no cross-reactivity with alachlor.

A particularly preferred hybridoma cell line, which synthesises and secretes into the surrounding medium a monoclonal antibody which has high specificity and affinity for metolachlor and shows a cross-reactivity with the best known structurally related metolachlor analogues of <10%, but especially of <2% and very particularly preferably of <0.1%.

A very particularly preferred hybridoma cell line is one which has the characterising features of ECACC 9002 1701, and the clones and subclones thereof.

Likewise embraced by the present invention are variants and mutants of the hybridoma cell lines previously characterised in detail, which arise spontaneously or else can be prepared artificially by means of known methods and which still have the characteristic properties of the starting material, that is to say they are still able to produce and secrete into the surrounding medium the antibodies according to the invention or derivatives thereof.

Likewise embraced by the present invention are methods for preparing said hybridoma cell lines and methods for preparing said monoclonal antibodies.

By clones and subclones of hybridoma cell lines are meant hybridomas which result from repeated cloning from the initial clone and which still have the features of the initial clone which are essential to the invention.

This invention furthermore relates to a method for the immunological detection of metolachlor, for example in samples of soil, water or air and in biological material such as, for example, in plant or animal extracts, by using the monoclonal antibodies according to the invention.

Particularly preferred in this connection is a competitive ELISA which can be used as direct or as indirect immunoassay.

Likewise a component of the present invention are means for the qualitative and quantitative determination of metolachlor in the form of test kits which are ready to use and which contain at least one of the monoclonal antibodies according to the invention as reagent and which are suitable for use under field conditions for rapid and reliable detection of metolachlor.

The monoclonal antibodies according to the invention are prepared using methods known per se, which are based essentially on the methods developed by Köhler and Milstein (*Nature*, 256: 495–497, 1975).

Since the target substance metolachlor which is to be analysed and for which specific monoclonal antibodies are to be developed is a relatively small and simple molecule which is not able on its own to induce an appropriate immune response in an experimental animal after administration thereto, it is necessary first to apply preparatory measures before the actual immunisation.

Compounds of this type, which are not able to induce an immunological reaction because of their size and simple structure, are called haptens or incomplete antigens and are thus contrasted with the complete antigens (=immunogens) which act both as antigen and are able to induce an immune response. Hapten molecules of this type can be conjugated with high molecular weight compounds (carrier molecules) which makes their properties comparable with those of complete antigens, that is to say they now have the ability to induce an immune response.

Some of the antibodies formed during the course of the immunisation reaction are then able to react with specific epitopes on the hapten molecule, irrespective of whether the hapten molecule is on its own or remains coupled to the carrier molecule.

The term hapten which is frequently used hereinafter is intended to mean within the scope of this invention primarily the metolachlor molecule used for the immunisation.

Thus, within the scope of this invention, the metolachlor acting as hapten is, before the immunisation of experimental animals, coupled to a high molecular weight carrier which is suitable for conferring complete antigenic activity on said metolachlor.

Suitable carrier molecules within the scope of this invention are primarily macromolecular compounds which have reactive groups which are freely accessible for the coupling reaction with the hapten and which are able by coupling to the hapten to confer on the latter an immunogenic potency or to enhance the immunogenicity thereof which is already present.

Particularly preferred within the scope of this invention are macromolecular compounds which contain freely accessible reactive amino groups.

Very particularly preferred as carrier molecule for the use according to the invention are lysine-rich proteins with a molecular weight between 10,000 and 1,500,000, such as, for example, bovine serum albumin (BSA: MW 66,200), human serum albumin (HSA,; MW 58,000) or keyhole limpet hemocyanin (KLH; MW>1,000,000), which can be obtained commercially and thus are available in any required amount.

It is, of course, also possible within the scope of the present invention to use other macromolecular compounds as carrier molecules as long as they meet the abovementioned requirements, such as, for example, porcine thyroglobulin, B2 microglobulin, hemocyanin, immunoglobulins, toxins (cholera, tetanus, diphtheria toxins etc.), polysaccharides, lipopolysaccharides, natural or synthetic polyadenylic and polyuridylic acids, polyalanyl and polylysine polypeptides or cell membrane components such as, for example, formalin- or glutaraldehyde-treated erythrocyte cell membranes.

Likewise suitable for use as carrier molecule in the method according to the invention is, for example, the purified or IgG fraction against mouse IgG (H+L) from rabbits according to the method described by H Kawamura and J A Berzofsky (*J. Immunol.*, 136: 58, 1986).

The conjugation of the hapten to the carrier molecule can take place either directly or else, preferably, via a bridging element which is, where appropriate, initially attached to the hapten molecule.

The substance to be analysed must be coupled to the carrier molecule for this purpose in such a way that the relevant structural elements of the target substances remain freely accessible and thus are able to induce a specific immune response, that is to say to induce the production of specific antibodies.

Compounds primarily suitable as bridging elements for conjugation of the hapten (metolachlor) to the carrier molecule are those which contain at least one or else several reactive groups which are able to interact with the freely accessible reactive groups of the carrier molecule.

It is particularly preferred within the scope of this invention to use bridging elements which comprise between 3 and 10 bridging C atoms and which have as reactive group(s) one or more reactive groups such as, for example, amino, carboxyl or SH group(s). These reactive groups can be reacted by methods known per se with the reactive groups of the hapten and carrier molecule to form a hapten-carrier conjugate.

It is thus possible, for example, to link a bridging element via a reactive amino group by means of dialdehydes (for example glutaraldehyde) to one of the free amino groups of the carrier molecule.

If the bridging element has a reactive SH group, the conjugation of the hapten to the carrier molecule can be carried out with free SH groups on the carrier by an oxidation.

It is particularly preferred within the scope of this invention to use bridging elements with a carboxyl group which can be linked to a free amino group of the carrier molecule with the aid of water-binding agents such as, for example, a carbodiimide, preferably N,N'-dicyclohexylcarbodiimide.

In order to couple the antigen to the carrier protein it is thus initially necessary to prepare a metolachlor derivative which is capable of this coupling.

Metolachlor derivatives which can be used within the scope of the present invention are especially those of the formula (I)

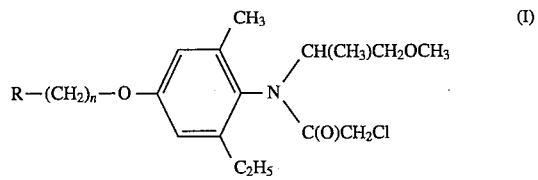

which have in the 4 position with respect to the amino functionality of metolachlor an R—$(CH_2)_n$—O— group in which R represents COOH, $NH_2$ or SH, but especially represents COOH, and n represents an integer from 1 to 10, preferably from 1 to 6.

Metolachlor derivatives of the formula I capable of coupling to a carrier molecule can be prepared by N-acylation of a compound of the formula II

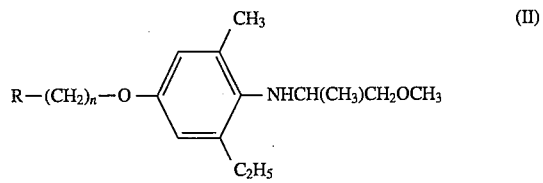

in which R and n have the meanings indicated for formula I, with a chloroacetic acid derivative which is capable of N-acylation, expediently in a solvent which is inert to the reaction, preferably under mild conditions [−10° C. to +30° C.].

Suitable N-acylating agents are reactive chloroacetic acid derivatives, especially acid halides [for example chloroacetyl chlorides and bromides], esters and anhydrides. It is advantageous in this reaction to trap the liberated acid by a suitable binder. Suitable for this are, for example, organic bases, such as trialkylamines [trimethylamine, triethylamine etc.], pyridine and pyrimidine bases or inorganic bases such as oxides, hydroxides [for example NaOH or KOH], bicarbonates, carbonates or hydrides of alkali metals and alkaline earth metals. It is expedient to carry out the reaction in the presence of 2 equivalents of the binder [based on product I]; catalysts which can be used for this purpose are 4-dialkylaminopyridines.

Compounds of the formula II are prepared in analogy to the procedure indicated diagrammatically hereinafter for N-chloroacetyl-N-(1-methyl-2-methoxyethyl)-2-methyl-4-(4'-hydroxycarbonylbutoxy)-6-ethylaniline.

A preferred example of a metolachlor derivative suitable for coupling to a carrier molecule is N-chloroacetyl-N-(1-methyl-2-methoxyethyl)-2-methyl-4-metolachlor derivative is N-chloroacetyl-N-(1-methyl-2-methoxyethyl)-2-methyl-4-(4'-hydroxycarbonylbutoxy)-6-ethylaniline which can be prepared as described in detail hereinafter in a 6-stage process starting from 3-ethyl-4-nitroso-5-methylphenol. The initial phenol is known or can be prepared in analogy to known phenols of similar structure.

The resulting metolachlor derivative capable of coupling is new and represents, owing to this specific coupling ability, a valuable starting material for the preparation of monoclonal antibodies with specificity for metolachlor. It is therefore an important constituent of the present invention.

The actual coupling reaction is preferably carried out using the active ester method. This entails the metolachlor derivative initially being solubilised in a suitable solvent. Particularly suitable solvents are aprotic solvents which have a low evaporation rate such as, for example, N,N-dimethylformamide (DMF) or dimethyl sulfoxide (DMSO).

The carboxyl groups are subsequently derivatised to an active ester by reacting the previously solubilised metolachlor derivative for example with N-hydroxysuccinimide, N-hydroxysulfosuccinimide, N,N'-dicyclohexylcarbodiimide or N,N'-carbonyldiimidazole or with derivatives of these compounds.

The active ester is then removed from the reaction mixture and added to BSA or KLH. After an incubation time of 0.1 to 12 hours, preferably of 3 to 5 hours, the precipitate is removed. The supernatant can then be used, where appropriate after interpolation of further purification steps, for the actual immunisation reaction.

Besides the active ester method which is preferred within the scope of this invention, it is also possible to use alternative methods for the coupling of the hapten to the carrier molecule, such as, for example, the mixed anhydride method. This entails the carboxyl group of the bridging element being linked to the carrier molecule by use of acetic anhydride or of the carbodiimide derivative 1-ethyl-3-(3'-dimethylaminopropyl)carbodiimide.

The donor animals are immunised by administration one or more times of a hapten which is coupled to a high molecular weight carrier molecule. Administration 2 to 3 times is particularly preferred, which is carried out at intervals of 7 to 30 days, but especially of 12 to 16 days.

The administration form preferred within the scope of the present invention is injection, which can be carried out both intravenously, intraperitoneally or subcutaneously. A combination of subcutaneous and intraperitoneal injection is preferred. In this case, the antigen (metolachlor conjugate) is present in a suitable buffer such as, for example, a PBS buffer which contains one of the conventionally used adjuvants. It is particularly preferred within the scope of this invention to use Freund's adjuvant.

An eventless period of 0.5 to 4 months is followed by another single administration of the hapten conjugate in a dose of 100 µg to 1000 µg.

In a period of 1 to 6 days after the last dose the donor animals are sacrificed and a spleen cell suspension is prepared.

This entails the isolated spleen cells being suspended in a suitable buffer (for example a BSS buffer) and stored in the form of a cell suspension until they are fused with suitable myeloma cells.

These fusions were initially complicated by the fact that the myeloma cell lines also synthesised monoclonal antibodies so that the hybrid produced two types of monoclonal antibodies, one with its origin in the myeloma cell and a second determined by the genetic information of the immunocompetent cell.

Thus, the tumour cells preferably used within the scope of the present invention are those which themselves are unable to produce monoclonal antibodies, such as, for example, SP2/0-Ag14 (Shulman et al, 1978) or X63-Ag8.653, which very greatly simplifies the analysis of the resulting fusion products. It is advantageous for the success of fusion if the spleen cells are present in an excess of 2 to 20 fold in relation to the myeloma cells.

The fusion of spleen and myeloma cells is carried out in a special fusion medium which has the composition which provides conditions which are optimal for the intended cell fusion.

Said fusion medium is preferably a buffer solution which contains one of the fusion promoters customarily used for fusing cells, such as, for example Sendai viruses or other paramyxoviruses, where appropriate in UV-inactivated form, calcium ions, surface-active lipids such as, for example, lysolecithin or polyethylene glycol. It is particularly preferred within the scope of this invention to use polyethylene glycol (PEG), especially polyethylene glycol (PEG) with an average MW of 600 to 6000, and in a concentration of 30% to 60%. A PEG concentration of 40%–50% is particularly preferred. The optimal fusion temperature is between 18° C. and 39° C. A temperature of 37° C. is particularly preferred.

After the fusion of the immunocompetent spleen cells with the myeloma cells has taken place, the fused antibody-producing hybrid cells are selected by methods known per se. Various possibilities exist for selecting successful fusion events (hybrid cells) from the 2 types of parent cells. One million or more cells of each parent type are routinely used in the fusion protocol. Since the fusion rate is not 100% it may be a difficult undertaking to separate the fusion products from the large excess of unfused or self-fused parent cells.

As already mentioned previously, the hybridoma cells are produced by fusion of short-lived antibody-producing (spleen) B cells and long-lived myeloma cells. The required result is a long-lived cell line which produces antibodies. Since the spleen cells have only a limited life span in the culture, it is therefore possible in principle simply to wait until unfused and all self-fused spleen cells have died. However, after this there still remains the task of separating the long-lived antibody-producing cells from the long-lived cells which do not produce antibodies.

A conventional selection system is based on the availability or non-availability of the enzyme hypoxanthine-guanine phosphoribosyltransferase (HGPRT). This enzyme is a constituent of the purine salvage pathway in mammalian cells. These cells are also furthermore able to synthesise purines de novo.

In normal circumstances it is probable that both synthetic routes operate in parallel to a certain extent.

However, if a cell has no HGPRT, the salvage pathway is blocked and the purines must be prepared from non-purine material.

Used as a rule for the selection of HGPRT-negative myeloma cells are so-called purine antimetabolites such as, for example, 8-azaguanine which has a very similar structure to the purine guanine and is therefore able to replace the latter in some of its normal reactions.

Azaguanine is incorporated in the DNA, which leads to impairment of normal growth behaviour and finally to death of the cell. Since azaguanine must be replaced via the salvage pathway, all those cells which have no HGPRT activity are unable to utilise azaguanine and thus grow in its presence.

A selective system which operates with the same enzyme but with the opposite sign, in that HGPRT-positive cells are selected in this case, has been described by J. W. Littlefield (1964).

This selection system is based on the use of the so-called HAT medium which contains, inter alia, hypoxanthine, aminopterin and thymidine (HAT medium) as constituents. Aminopterin is an antimetabolite which inhibits the de novo purine synthesis as well as the methylation of deoxyuridylate to thymidylate.

Hypoxanthine can act as alternative purine in the case where aminopterin blocks de novo purine synthesis, while thymidine makes methylation of deoxyuridylate unnecessary.

Hence, in the presence of aminopterin, all HGPRT-positive cells will proliferate, while HGPRT-negative cells die.

In the hybrid system which is used for the selection within the scope of this invention, the myeloma cells are preferably resistant to azaguanine and sensitive to aminopterin, that is to say they are HGPRT-negative. The antibody-producing cells are, by contrast, HGPRT-positive.

It is possible by fusion of the cells and cultivation in an HAT medium to select the cells which have fused together successfully because the myeloma cells, which are responsible for the proliferation, are able to grow only in the presence of an HGPRT activity and this activity must be provided by the HGPRT-positive cell line.

It is true that the HGPRT-positive antibody-producing cell lines are not killed in this medium. However, they survive for only a certain time and are unable to proliferate.

Thus fusion of the cells in an HAT medium provides a system in which although the myeloma cells and the antibody-producing cells are able to grow for a period which suffices for the production of hybrid cells, only the hybrid cells are able to survive and proliferate.

In a particular embodiment of the present invention, the fused hybrid cells are cultivated in the presence of macrophages isolated previously from the peritoneum of untreated, non-immunised experimental animals, so-called feeder cells. For cultivation and selection of the fused hybrid cells, the cell suspension is divided into several aliquots and the individual aliquots are continually investigated for the development of hybrid cell cultures and for the production of antibodies.

It is particularly preferred within the scope of this invention to cultivate the fused hybrid cells on microtitre plates.

This entails the cell suspension obtained after the fusion being distributed over the individual wells of a microtitre plate and cultivated for a period of 7 to 30 days under suitable conditions which promote the growth of the fused hybrid cells (for example HAT/HT media).

The supernatants of hybrid cultures which have grown are continually investigated for the production of antibodies.

Positive hybrid cell cultures are then singled out using known methods, but preferably using the limiting dilution method, and subsequently cloned in suitable cultivation media.

The supernatants from the cell clones which have grown are likewise tested for the production of antibodies.

The hybridoma cell clones according to the invention prepared as described are screened for the production of suitable monoclonal antibodies preferably using one of the immunoassays conventionally used for this purpose, such as, for example, an enzyme-coupled immunoassay or a radio-immunoassay.

In the enzyme-coupled immunoassay, the hapten conjugates which have been characterised in detail previously are initially adsorbed onto a solid support. The remaining free binding sites are then saturated by adding carrier molecules and thus blocked.

To detect monoclonal antibodies, aliquots of the supernatants of said hybridoma cell clones are incubated with the carrier-bound hapten conjugates.

The present invention further relates to the preparation of monoclonal antibodies by using methods known per se, which are characterised in that the hybridoma cell lines according to the invention which have been characterised in detail previously, or else clones or subclones thereof, which synthesise and secrete into the surrounding medium the antibodies according to the invention are cultivated in vitro or in vivo by means of known methods.

The in vitro cultivation of the hybridoma cells according to the invention is carried out in suitable cultivation media, especially in the customarily used standardised culture media such as, for example, Dulbecco's modified Eagle medium (DMEM) or RPMI 1640 medium, each of which can be supplemented where appropriate by adding mammalian sera such as, for example, fetal calf serum, or by growth-promoting additives and trace elements.

The isolation of the monoclonal antibodies preferably starts with a precipitation of the immunoglobulin fraction from the particular supernatants of the hybridoma cultures, for example by using ammonium sulfate. This is followed by further working up and purification steps which are known to those skilled in this an and which include, for example, the use of chromatographic methods such as, for example, gel filtration, ion exchange chromatography, DEAE-cellulose chromatography, protein A or immunoaffinity chromatography.

However, it is also possible to obtain large amounts of the monoclonal antibodies according to the invention using in vivo methods.

Thus, for example, it is possible to inject antibody-producing hybridoma cell clones into suitable mammals, which induce the development of antibody-producing tumours in the treated animals. After a period of 1 to 3 weeks, the antibodies can be isolated from the body fluids of the animals treated in this way.

In a particular embodiment of the present invention, female Balb/c mice which have been pretreated, where appropriate, with a hydrocarbon such as, for example, pristane receive intraperitoneal injection of a hybridoma cell clone according to the invention. One to three weeks after the injection of the hybridoma cell clone the ascites fluid is collected and stored until worked up further.

The monoclonal antibodies are isolated in a manner exactly analogous to the previously described isolation from the supernatants of hybridomas cultivated in vitro.

The present invention further relates to the use of the antibodies according to the invention in one of the conventional immunoassays for detecting metolachlor and for differentiating metolachlor from structurally related compounds, but especially from the metolachlor analogue alachlor in samples of soil, air and water and, where appropriate, in extracts from plants or other biological material.

The monoclonal antibodies according to the invention can thus be used in all known immunoassays which am based on the specific binding between antigen and the corresponding monoclonal antibody, such as, for example, in a radioimmunoassay (RIA), an enzyme-coupled immunoassay (ELISA), an immunofluorescence test etc.

The monoclonal antibody according to the invention can be used as such or else in the form of a radioactively labelled derivative in the RIA test. In this connection it is possible to use all modifications hitherto known of the RIA test for detecting the target substances relevant within the scope of this invention, such as, for example, an RIA test in homogeneous or solid phase, a heterogeneous RIA test and a single or double (sandwich) RIA test with direct or indirect (competitive) detection of the antigen. The same also applies to the use of an enzyme-coupled immunoassay.

It is preferred within the scope of this invention to use a monoclonal antibody according to the invention in a competitive immunoassay for detecting metolachlor The competitive immunoassay principle is based on a competition between a labelled antigen, or an antigen which is bound to a solid support, and a free antigen for the relevant binding sites on the antibody molecule.

A distinction is made in principle between two possibilities for carrying out this competitive immunoassay.

a) The first method is based on the competition between the antigen which is bound to a solid support and the free antigen for the free binding sites on the antibody which is provided with a label. In this connection, the binding of the antigen to a solid support can take place either directly or else via a carrier molecule.

In this case, the concentration of free antigen is determined via the decrease in the labelled antibody which is bound to the antigen immobilised on the support.

This decrease is proportional to the amount of free antigen contained in the sample.

b) An alternative method is based on the fact that free and labelled antigen compete with one another for the relevant binding sites on the antibody which, in this case, is bound to a solid support.

The concentration of free antigen is determined via the decrease in labelled antigen, which decrease varies as a function of the concentration of free antigen.

Examples of solid support material suitable for the binding of the antigen or of the antibody are the plastic surface of a microtitre plate or of a test tube, the surface of beads made of polystyrene, polypropylene, polyvinyl chloride, glass or plastic or else the surface of strips of filter paper, dextran, cellulose or nitrocellulose, or similar materials. The latter are coated with one of the monoclonal antibodies according to the invention or with an antigen, it being possible for the binding to the support material to be brought about by simple adsorption or else, where appropriate, after preceding activation of the support material with, for example, glutaraldehyde or cyanogen bromide.

It is particularly preferred within the scope of this invention to use the monoclonal antibody according to the invention in an enzyme-coupled immunoassay [ELISA ('Enzyme Linked Immuno Sorbent Assay)]. This may entail the monoclonal antibody according to the invention being used as such or in the form of an enzyme-coupled derivative.

The ELISA assay is based either on the use of an enzyme-coupled derivative of the antibody according to the invention or else of enzyme-coupled antibodies which are known per se and which recognise and bind to an epitope of an antibody according to the invention.

It is particularly preferred within the scope of this invention to use an indirect ELISA assay in which one of the support materials described previously initially coated with an antigen, especially a conjugate of hapten and a high molecular weight carrier molecule such as, for example, BSA or KLH. Preferred within the scope of the present invention is a conjugate concentration of 10 ng/100 µl of buffer to 200 ng/100 µl of buffer, preferably of 30 ng/100 µl of buffer to 100 ng/100 µl of buffer and very particularly preferably of 40 ng/100 µl of buffer to 60 ng/100 µl of buffer.

The carrier-bound antigen is subsequently incubated with a test solution which contains the antigen to be detected and one of the antibodies according to the invention. The antigen to be detected can in this connection be present either in free form or else as constituent of a sample of water or soil.

After having an incubation time of 10 minutes to 2 hours, the complete mixture is incubated with an enzyme-labelled antibody which recognises and binds to the monoclonal antibody according to the invention. One example of an enzyme-labelled antibody of this type is a phosphatase-labelled goat anti-sheep immunoglobulin, or a corresponding goat anti-mouse antibody, both of which can be obtained commercially.

The amount of bound antibody protein can be determined by means of an enzyme-substrate reaction, for example using spectroscopic methods.

Likewise preferred within the scope of this invention is a direct ELISA test which is based on the competition of labelled and free antigen for the antibody bound to one of the abovementioned support materials.

The antigen can be labelled by means of known methods using the labels customarily used in immunological diagnosis. Preferred within the scope of the present invention is the use of an enzyme label such as, for example, of alkaline phosphatase, which is linked to the antigen to be detected.

The proportion of free antigen present in a particular sample can then be determined very simply on the basis of the decrease in labelled antigen, which decrease becomes greater as the amount of free antigen contained in the sample rises.

The present invention further relates to means for the qualitative and quantitative determination of metolachlor in the form of a test kits which can, besides the monoclonal antibodies according to the invention and/or their derivatives, contain, where appropriate in addition, other monoclonal or polyclonal antibodies, but especially labelled monoclonal or polyclonal antibodies, and further additives.

Particularly preferred within the scope of this invention are test kits which are based on one of the customarily used immunoassays selected from the group consisting of radioimmunoassay, enzyme-coupled immunoassay and chemiluminescence assay. Very particularly preferred test kits are those in which the detection of metolachlor is based on a competitive immunoassay, but especially on an enzyme-coupled direct or indirect immunoassay (ELISA).

Test kits for a radioimmunological detection of metolachlor, can contain, for example, the following constituents:

(a) a suitable support material which can be uncoated or else coated with one of the antibodies according to the invention or with an antigen conjugate;

(b) where appropriate freeze-dried or concentrated solutions of one of the antibodies according to the invention and/or of a radioactively labelled derivative thereof or radioactively labelled antigen or standardised solutions of the antigen;

(c) buffer solutions and (d) where appropriate polypeptides, detergents and further additives which, for example, prevent non-specific adsorption and aggregate formation, and (e) pipettes, reaction vessels, calibration plots, package inserts etc.

Test kits for the immunological detection of metolachlor based on an enzyme-coupled immunoassay (ELISA) can contain, for example, the following constituents:

(a) a suitable support material which can be uncoated or else coated with one of the antibodies according to the invention or with an antigen conjugate;

(b) where appropriate freeze-dried or concentrated solutions of one of the antibodies according to the invention and/or of a second enzyme-labelled monoclonal or polyclonal antibody which is directed against the antigen to be determined or against an antibody recognising the antigen;

(c) enzyme substrates in solid or dissolved form;

(e) the antigen or standardised solutions of the antigen;

(f) buffer solutions;

(g) where appropriate polypeptides, detergents and further additives which, for example, prevent non-specific adsorption and aggregate formation, and (h) pipettes, reaction vessels, calibration plots, colour tables, package inserts etc.

A test kit for the detection of metolachlor which is based on a chemiluminescence test can contain, for example, the following constituents:

(a) a suitable support material which can be uncoated or else coated with one of the antibodies according to the invention or with an antigen conjugate;

(b) where appropriate freeze-dried or concentrated solutions of one of the antibodies according to the invention and of a second polyclonal antibody which is able to recognise the first antibody according to the invention and is linked to a chemiluminescent label;

(c) solutions containing a component which induces the emission of light, such as, for example, $H_2O_2$ and NaOH;

(d) buffer solutions;

(e) where appropriate polypeptides, detergents and further additives which prevent non-specific adsorption and aggregate formation and (f) pipettes, reaction vessels, package inserts etc.

Support materials which can be used within the scope of the present invention primarily comprise insoluble polymeric materials selected from the group consisting of polystyrene, polyethylene, polypropylene, polyesters, polyacrylonitrile, polyvinyl chloride, polyacrylamide, nitrocellulose, crosslinked dextran, fluorinated resins, agarose, crosslinked agarose, polysaccharides etc. However, besides these, other materials are also conceivable, such as, for example, glass, metal, nylon-based net fabric etc.

The specific abovementioned support materials can have a wide variety of designs and, depending on the particular intended specific purpose of use, very different types of shapes. The latter comprise, for example, dishes, spheres, plates, rods, cells, vials, tubes, fibres, nets etc.

Frequently used for producing test kits are, for example, microtitre plates made from transparent plastic materials such as, for example, polyvinyl chloride or polystyrene, which can be uncoated or else coated with one of the antibodies according to the invention, with free antigen or with an antigen conjugate. Also used are beads, tubes or rods of polystyrene and polystyrene latex, in which case the surrounding latex material can be separated from the polystyrene particles by centrifugation.

Another component of the test kit according to the invention comprises labels or indicators which make it possible to detect the presence of a complex-forming reaction, but especially of an immunological reaction, which preferably results in an antigen-antibody complex or else in a ligand-receptor complex, in which case where appropriate quantitative information, besides qualitative, may be gained about the antigen to be detected. Suitable labels or indicators are both single atoms and molecules, which can be involved either directly or else indirectly in the generation of a detectable signal. These labels or indicators can be either linked directly to the antigen to be detected or to one of the monoclonal antibodies according to the invention, or else incorporated in the latter. However, they can also be in the form of single substances or of a component of a separate compound which is neither itself the antigen to be detected nor one of the monoclonal antibodies according to the invention but which in turn is able to react with the receptor molecule, for example in the form of a complex formation.

These separate compounds preferably take the form of a second antibody molecule which can be both monoclonal and polyclonal in origin, of a complement protein or fragments thereof, of *S. aureus* protein A etc. These separate compounds recognise and bind specifically to a receptor molecule such as, for example, the antigen to be detected or one of the monoclonal antibodies according to the invention, but preferably to a receptor molecule which is present in the form of a complex.

In many cases there is a need for further additional reagents which then lead to a detectable signal only on cooperation with the label. This particularly applies when enzymes are involved.

Labels or indicators which can be used within the scope of the present invention are very well known to the person skilled in the art of immunology and immunochemistry. They comprise, for example, radioactively labelled elements or substances, enzymes or chemiluminescent substances. The following list of possible labels or indicators is intended merely to these to illustrate the wide variety of substances and reagents which can be used by way of example but without thereby restricting the subject-matter of the invention in any way.

Examples of suitable labels or indicators may be found within the group of radioactive elements. Particularly preferred elements in this connection are those which either themselves emit γ rays, such as, for example, $^{124}I$, $^{125}I$, $^{128}I$, $^{132}I$, $^{51}Cr$ or else induce emission of these rays, such as, for example, $^{11}C$, $^{18}F$, $^{13}N$. Likewise suitable are so-called β-emitters such as $^{111}In$, $^{14}C$ and $^{3}H$.

Other suitable labels comprise chemiluminescent substances, but especially fluorescent substances, which can be linked very simply by chemical means to the antigen or to an antibody without denaturing the latter. The resulting fluorochrome can easily be detected using fluorometric methods. Worthy of specific mention at this point are fluorochromes selected from the group consisting of fluorescein isocyanate, fluorescein isothiocyanate, 5-dimethylamino-1-naphthalenesulfonyl chloride, tetramethylrhodamine isothiocyanate, lissamine, rhodamine 8200 sulfonyl chloride etc.

Further fluorescent agents and a description of analytical techniques are to be found in DeLuca, "Immunofluorescence Analysis", in: *Antibody As a Tool*, Marchalonis et al, John Wiley & Sons, Ltd., pp 189–231 (1982).

It is particularly preferred within the scope of this invention to use enzymes as labelling or indicator substances, such as, for example, horseradish peroxidase, alkaline phosphatase, β-D-galactosidase, glucose oxidase, glucoamylase, carbonic anhydrase, acetylcholinesterase, lysozyme, malate dehydrogenase, glucose-6-phosphate dehydrogenase etc. When enzymes are used as labelling substances it is necessary to add additional reagents which permit the formation of an immune complex to be followed via the enzyme activity and, where appropriate, a stop reagent with which the enzyme reaction can be stopped.

Particularly preferred in this connection are reagents which result in a colour reaction. In the case of horseradish peroxidase, an example which may be mentioned at this point is hydrogen peroxide which results, in combination with an additional oxidised dyestuff precursor such as, for example, diaminobenzidine or o-phenylenediamine, in a brown or yellow colour. When glucose oxidase is used as labelling substance it is possible to use, for example, 2,2'-azino-di-(3-ethyl-benzothiazoline-6-sulfonic acid) [ABTS] as substrate.

Thus the present invention further relates to the use of test kits which contain at least one of the monoclonal antibodies according to the invention as reagent, for the rapid and efficient, qualitative and/or quantitative detection of metolachlor and for differentiating metolachlor from the best known structurally related compounds, but especially from the metolachlor analogue alachlor.

I. NON-LIMITING EXEMPLARY EMBODIMENTS

Example 1: Synthesis of a metolachlor derivative 1.1: Preparation of N-chloroacetyl-N-(1-methyl-2-methoxyethyl)-2-methyl-4-(4'-hydroxycarbonylbutoxy)-6-ethylaniline which is able to couple to the carrier protein Stage 1: Preparation of 3-ethyl-4-nitroso-5-methylphenol 102 g (749 mmol) of 3-ethyl-5-methylphenol are introduced into 600 ml of ethanol. While stirring vigorously, 600 ml of concentrated hydrochloric acid are added dropwise, keeping the reaction vessel at room temperature by cooling. The reaction mixture is then cooled to 0° C. At this temperature, 77.5 g (1123.5 mmol) of sodium nitrite in 78 ml of deionised water are added dropwise. The resulting mixture is then stirred at 5° C. for 2 hours and subsequently poured into 3 liters of ice-water, when the title compound crystallises out. It is filtered off, washed several times with ice-water and recrystallised from methanol. Yield 88.7 g (71.8% of theory); melting point 138° C. (with decomposition).

Stage 2: Preparation of 3-ethyl-4-amino-5-methylphenol 88.7 g (537.6 mmol) of the 3-ethyl-4-nitroso-5-methylphenol prepared in stage 1 are catalytically hydrogenated in 1 liter of tetrahydrofuran (THF) with molecular hydrogen under 5 bar at 20°–25° C. 10 g of 5% palladium on active charcoal (Pd-C) are used as catalyst. The hydrogen uptake is 77% of theory. The catalyst is filtered off, the filtrate is evaporated and the residue is recrystallised from methanol. Yield 51.2 g (63.2% of theory); melting point 167°–170° C.

Stage 3: Preparation of 2-methyl-4(4'-ethoxycarbonylbutoxy)-6-ethylaniline 500 ml of dimethyl sulfoxide (DMSO) are introduced at room temperature and, while stirring vigorously, 52.1 g (338.6 mmol) of the 3-ethyl-4-amino-5-methylphenol prepared in stage 2 are added in small portions. The mixture is cooled to 15° C. Then 33.5 g (507.9 mmol) of aqueous 85% strength potassium hydroxide solution are added dropwise so that the reaction temperature does not exceed 20° C. Then 82.7 ml (507.9 mmol) of ethyl 5-bromovalerate are added dropwise over the course of 70 minutes, maintaining the reaction temperature at 25° C. After a homogeneous solution has formed it is added to a mixture of 130 ml of 4M hydrochloric acid and ice and stirred well. The aqueous mixture is washed with diethyl ether. The aqueous phase is then made alkaline with 2M NaOH and extracted with diethyl ether, and the ether phase is washed twice with water and then with saturated brine, dried over sodium sulfate and concentrated. 67.5 g of a viscous oil are obtained and purified by vacuum distillation. Yield 31.7 g (33.7% of theory), boiling point 151°–152° C./$10^{-2}$ Torr.

Stage 4: Process for the preparation of N-(1-methyl-2-methoxyethyl)-2-methyl-4-(4'-ethoxycarbonylbutoxy)-6-ethylaniline 30.4 g (108.8 mmol) of the 2-methyl-4(4'-ethoxycarbonylbutoxy)-6-ethylaniline prepared in stage 3 are dissolved in 300 ml of methanol, and 0.3 g of concentrated sulfuric acid is added. 20 g (163.2 mmol) of 72% strength methoxyacetone in 100 ml of methanol are added dropwise to the stirred solution under room temperature (RT). This is followed by catalytic hydrogenation with molecular hydrogen. 1.5 g of 5% palladium on active charcoal is used as catalyst. After 8 hours under 5 bar and at temperatures of 40°–45° C. the hydrogen uptake is 106% of theory. The catalyst is filtered off; the residue is taken up in diethyl ether; the ether phase is washed successively with sodium bicarbonate solution, ice-water and saturated brine, dried over sodium sulfate and evaporated. Yield 29 g (75.9% of theory) in the form of a viscous pale brown oil.

Stage 5: Preparation of N-(1-methyl-2-methoxyethyl)-2-methyl-4-(4'-hydroxycarbonylbutoxy)-6-ethylaniline 19 g (54 mmol) of the N-(1-methyl-2-methoxyethyl)-2-methyl-4-(4'-ethoxycarbonylbutoxy)-6-ethylaniline prepared in stage 4 are mixed at room temperature with 150 ml of 2M potassium hydroxide solution. The resulting emulsion is left to react to completion by stirring at room temperature for about 20 hours. The reaction mixture is then adjusted to pH 7 with hydrochloric acid and extracted twice with diethyl ether. The ether phases are combined, washed several times with saturated brine, dried over sodium sulfate and evaporated. Yield 12.9 g (73.9% of theory)$n_D^{23}$ 1.517, viscous oil.

Stage 6: Preparation of N-chloroacetyl-N-(1-methyl-2-methoxyethyl)-2-methyl-4-(4'-hydroxycarbonylbutoxy)-6-ethylaniline 9.9 g (30.6 mmol) of the N-(1-methyl-2-methoxyethyl)-2-methyl-4-(4'-hydroxycarbonylbutoxy)-6-ethylaniline prepared in stage 5 are dissolved in 400 ml of methylene chloride and, while stirring at room temperature, 30.6 ml (30.6 mmol) of 1M sodium hydroxide solution are added.

2.7 ml (33.67 mmol) of chloroacetyl chloride are slowly added dropwise, while stirring, at temperatures between 20° and 25° C. The reaction mixture is stirred for approximately a further 2 hours. Subsequently, again under the abovementioned conditions, 10.2 ml of 1M sodium hydroxide solution and then 0.9 ml of chloroacetyl chloride are added and the mixture is stirred further at room temperature for about 12 hours. The resulting mixture is made basic and extracted with diethyl ether, the ether phase is discarded and the aqueous phase is adjusted to pH 3 with hydrochloric acid. The aqueous phase is again extracted with diethyl ether, washed with ice-water and saturated brine several times, dried over sodium sulfate and evaporated. Yield 7.2 g (59% of theory) viscous oil, $n_D^{23}$ 1.515. The structure of compound 6 is confirmed by mass-spectrometric methods [Finnigan 4500 with direct exposure probe (DEP)].

Diagrammatic representation of the preparation of the N-chloroacetyl-N-(1-methyl-2-methoxyethyl)-2-methyl-4-(4'-hydroxycarbonylbutoxy)-6-ethylaniline which is able to-couple to the carrier protein

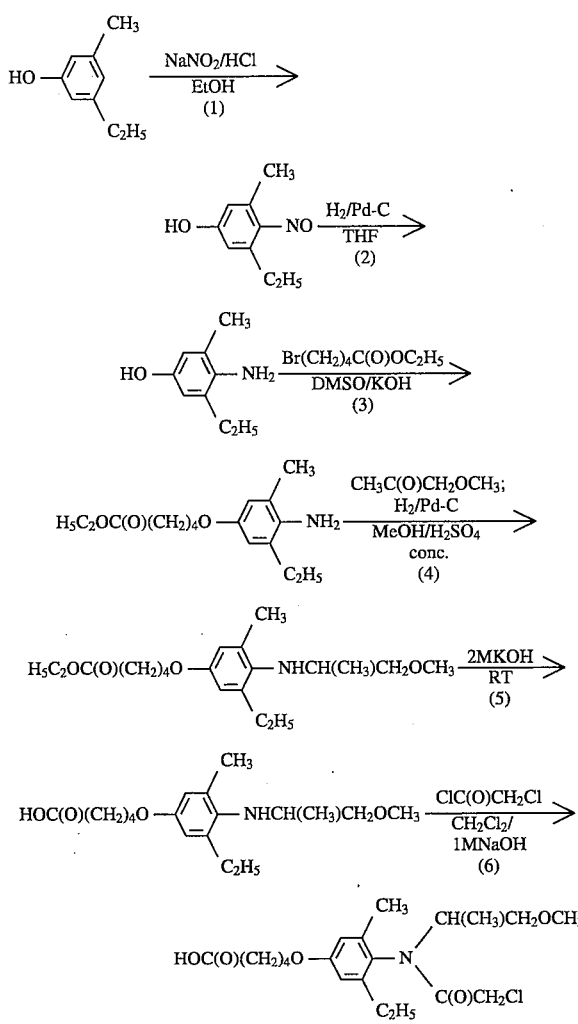

1.2: Metolachlor-protein conjugate

The metolachlor derivative prepared as in Example 1 is conjugated either to bovine serum albumin (BSA; Fluka) or to keyhole limpet hemocyanin (KLH; Calbiochem) using the activated ester method (Kulkarni et al., 1981).

This specifically entails the carboxyl group of the derivative being solubilised in N,N-dimethylformamide (DMF) (8 mg/200 µl) at room temperature and subsequently mixed with a 4 molar excess of α-hydroxysuccinimide (9.1 mg/200 µl of DMF) and N,N'-dicyclohexylcarbodiimide (16 mg/200 µl of DMF). The reaction mixture is stirred initially at 22° C. for 1 hour and then at 4° C. for 18 hours.

The white precipitate formed in the reaction is removed by centrifugation at 12,000 g at room temperature for 3 minutes, and the activated ester is then added to BSA or KLH (24 mg) which has previously been solubilised in 5.4 ml of a phosphate-buffered saline [PBS buffer, 0.01M sodium phosphate and 0.145M NaCl, pH 7.0]. The molar ratio of [derivative]/[BSA] is about 55/1 (8 mg of derivative/ 24 mg of BSA) in this case.

After incubation at a temperature of 4° C. for 4 hours, the precipitate which has formed is removed by centrifugation at 2000 g and at 4° C. for 10 minutes, and the remaining supernatant with the protein conjugate is extensively dialysed against PBS [containing 3 mM NaN$_3$] before it is then used for the immunisation experiments.

The extent of the coupling reaction is determined by SDS gel electrophoresis and by absorption spectrophotometry at 280 nm, which corresponds both to the UV peak of BSA and to that of compound 6 [$A_{max}$=274 nm]. The molar ratio of metolachlor to BSA is about 23:1.

1.3: Conjugation of the hapten to alkaline phosphatase

16 µg of the active ester of N-chloroacetyl-N-(1-methyl-2-methoxyethyl)-2-methyl-4-(4'-hydroxycarbonylbutoxy)-6-ethylaniline prepared as in Example 1.2 are added to 40 µl of alkaline phosphatase from calf intestine (153 µg/230 U) [Calbiochem, EIA grade]. After incubation at 4° C. for 4 hours, the reaction mixture is extensively dialysed against PBS containing 3 mM NaN$_3$. The enzymatic activity of the conjugate is determined using p-nitrophenyl phosphate as substrate. The activity of the enzyme remains unchanged after the hapten conjugation.

Example 2: Immunisation

Groups each of 5 female BALB/c mice (Tierfarm Sisseln, Switzerland) which are between 4 and 6 weeks old receive 3 series of intraperitoneal or subcutaneous injections with KLH-conjugated metolachlor (50 µg/injection).

The first injection contains 0.1 ml of the conjugate in PBS, which is mixed in a ratio of 1:1 with 0.1 ml of complete Freund's adjuvant.

50 µl of this injection solution are injected intraperitoneally, and the remaining 150 µl subcutaneously.

In the second and third injection series, which is carried out 14 and 30 days, respectively, after the first administration, incomplete replaces complete Freund's adjuvant.

1 week after the last injection, blood serum is taken from the experimental animals, and the blood titre is determined by an ELISA test, the microtitre plates having previously been coated with BSA-conjugated hapten (see section 6).

After an eventless period of 2 months, another single intraperitoneal injection of the KLH conjugate is given in a dose of 370 µg/200 µl of PBS.

Example 3: Fusion protocol 3.1. Obtaining feeder cells (peritoneal macrophages)

Untreated Balb/c mice about 6 to 8 weeks old are sacrificed one day before the intended fusion and are sterilised by immersion in 70% strength alcohol.

Then sterile incisions are made in the fur and the upper abdominal skin without injuring the peritoneum. A sterile 5 ml plastic syringe and a sterile 18 gauge injection needle are used to inject 4 ml of BSS (without Ca$^{2+}$ and Mg$^{2+}$) and 1 ml of air into the abdominal cavity.

After the abdomen has been gently massaged (the syringe and needle remaining in the abdominal cavity), the previously injected BSS buffer is withdrawn again from the peritoneum and placed in a sterile Falcon tube. This procedure is repeated twice more. The macrophages obtained in this way are cooled in ice and subsequently washed 2× with 20 ml of BSS each time.

This entails the macrophages being centrifuged at 300 g at a temperature of 5° C. for 10 min each. The pellet is then resuspended in 50 ml of HAT medium, and the cell suspension is distributed over 4 Costar plates with a total of 24 wells (0.5 ml/well).

The macrophages prepared in this way are then stored in an incubator at a temperature of 37° C. and a CO$_2$ concentration of 6%.

About 4×10$^6$ macrophages are required for each fusion process.

3.2. Culture of the myeloma cell line Sp 2/0-Ag 14

The said myeloma cell line Sp 2/0-Ag 14 is a myeloma cell line which does not itself secrete antibodies and is described by M. Shulman et al. (1978). This myeloma cell line can be obtained from the American Type Culture Collection in Rockville, Md.

50 ml of a well grown culture which contains at least 10 million cells are required for each fusion. The myeloma cells are preferably cultivated in T 175 Falcon bottles (supplied by Beckton & Dickenson).

One day before the fusion, the cultivation medium (RPMI 1640) is replaced by fresh RPMI 1640 medium. On the day of fusion, the Sp 2/0-Ag 14 cells are harvested, placed in a sterile 50 ml plastic tube and centrifuged at 300 g and a temperature of 5° C. for 10 min (MSE centrifuge, model Chilspin, UK). After the centrifugation, the supernatant is aspirated off and discarded. The cells are washed 2× with about 30 ml of BSS buffer ($Ca^{2+}$ and $Mg^{2+}$ free) each time (10 min at 300 g, 5° C.) and then resuspended in 5 ml of BSS.

An aliquot of the cell suspension is removed for the determination of the cell count and is stained with fluorescein diacetate (FDA). The myeloma cells are stored on ice until used further.

3.3. Preparation of a spleen cell suspension

The spleen is removed from a Balb/c mouse which has previously been immunised as in Example 2 under sterile conditions and while cooling in ice.

The previously immunised Balb/c mouse is sacrificed by cervical dislocation, and the spleen is removed under sterile conditions. For this, the mouse is briefly immersed in 70% strength ethanol and dissected with sterile instruments. The spleen is carefully removed and placed on a fine nylon net. There it is cut up into small pieces with scissors and then carefully forced through the net, using a 5 ml syringe plunger, without destroying too many cells during this. The net is rinsed with BSS throughout the process.

The cell suspension obtained in this way is placed in 50 ml plastic tubes and centrifuged at 300 g and a temperature of 5° C. for 10 min (MSE centrifuge, model Chilspin; UK). The cells are then washed 2× with 20 ml of BSS each time (10 min.; 300 g; 5° C.; MES Chilspin) and the cell pellet after centrifugation is resuspended in 10 ml of BSS.

The spleen cells are left on ice until fused with Sp 2/0-Ag 14 myeloma cells.

3.4. Fusion: Spleen cells and Sp 2/0-Ag 14 myeloma cells

The ratio of myeloma cells to spleen cells for the fusion should be 1:10.

Spleen cells (in BSS buffer) and Sp 2/0-Ag 14 myeloma cells (in BSS buffer) are mixed in the stated ratio and centrifuged at 300 g and a temperature of 5° C. for 10 min (MSE centrifuge, model Chilspin). The pellet is again resuspended in BSS buffer and the suspension is then centrifuged again. The pellet is cautiously stirred up and placed in a water bath at 37° C. Then 1 ml of preheated and sterile PEG-4000 (MERCK) is added dropwise to the cells over a period of 60 sec, during which the entire mixture is continuously agitated. The cells are then shaken for a further 30 sec before 5 ml of a previously heated BSS buffer (without $Ca^{2+}$, $Mg^{2+}$) are likewise added dropwise over a period of about 5 min while stirring continuously.

The cells fused in the manner described are then spun down (10 min; 300 g; 20° C., MSE centrifuge, model Chilspin) and the supernatant is aspirated off and discarded. The cell pellet is resuspended in 50 ml of HAT medium, and the cell suspension obtained in this way is distributed over the prepared 4 Costar plates (microtitre plates with 24 wells, diameter of each well 24 mm; total area for cell growth 2.0 $cm^2$) (0.5 ml/well).

The Costar plates are incubated at a temperature of 37° C. and at a $CO_2$ concentration of 6%.

Example 4: Cultivation of the hybrid cells

On the 1st day after the cell fusion, 1 ml of HAT medium is added to each well of the culture plates. The fused cells are checked under the microscope 3 to 4 days after the cell fusion. At the same time, the used medium is aspirated off and replaced by 1 ml of fresh HAT medium. After a further 3 days (6–7 days after the cell fusion) the culture medium is changed again. From the 7th to the 10th day after the cell fusion each well is scanned under the microscope for hybrids, and the medium is renewed 2 to 3× a week.

As soon as hybrids have grown in a well, the HAT medium therein can be replaced by HT medium. The supernatant from washed hybrid cultures (at least 10% of the wells) is removed with a sterile Pasteur pipette and tested for the presence of antibodies.

As soon as the wells are covered with growth of positive hybrid colonies, the latter can be transferred to new Costar plates in RPMI 1640 medium, with the contents of a well covered in growth being distributed to 2 to 3 new wells.

Example 5: Cloning of the positive hybrid cells

Using a pipette, the cells in a positive well are dissolved and transferred in 1 ml of medium into a tube. An aliquot for determination of the cell count is then removed and stained with FDA (dilution 1:2 with FDA: 50 µl of cells+50 µl of dyestuff). The preferred cell count is $10^5$ to $10^6$ cells/ml. The hybrid cells are then diluted in a ratio of 1:100 with HT medium (for example 100 µl of cells+9.9 ml of HT medium).

25 ml of HT medium is placed in each of two 50 ml Falcon tubes and each tube is made up to a total of 30 ml with 5 ml of a macrophage suspension. The macrophages are previously isolated from a mouse and resuspended in 10 ml of HT medium (compare section 3.1).

The hybrid cells are diluted in these macrophage-containing Falcon tubes until a cell density of (i) 270 cells/30 ml or (ii) 90 cells/30 ml is reached. These mixtures are then distributed on Costar plates (microtitre plates with 96 wells), 200 µl being placed in each well. This corresponds to a cell count of (i) 1.8 cells/well or (ii) 0.6 cells/well. 1.5 microtitre plates are required in this way for each dilution.

After 7 days, the individual wells are checked under the microscope, and the wells which contain cell clones are noted. The dilution at which about 50% of the wells contain cell clones is used for the ELISA test. This ought, as a rule, to be the dilution with 0.6 cells/well.

After about 7–10 days the supernatants of the positive wells (with clones) are tested in an ELISA test for the presence of monoclonal antibodies, and the positive clones are grown in RPMI 1640 medium on Costar plates (with 24 wells). Aliquots of these positive clones are stored in liquid nitrogen.

Example 6: Hybridoma screening (ELISA test)

Initially 100 µl of a solution of BSA-conjugated hapten in sodium carbonate buffer (50 mM, pH 9.6) are placed in the individual wells of a microtitre plate, and this mixture is incubated at 4° C. in a humidity chamber overnight. The wells are then each washed 5× with a 0.1% PBS-Tween buffer. To block the unoccupied binding sites on the microtitre plate, 200 µl of a PBS-BSA solution (1%) are placed in each well. This mixture is incubated at room temperature for 1–2 hours and then washed with a 0.1% strength PBS-Tween buffer.

200 μl of the hybridoma supernatant which is diluted in the ratio 1:2 with PBS-Tween (0.1%) are then placed in each well, and the complete mixture is incubated at room temperature for 2 hours. The wells are then washed again 5× with a 0.1% strength PBS-Tween buffer.

This is followed by incubation with phosphatase-conjugated goat anti-mouse antibody (Kirkegaard & Perry Lab.). Initially 100 μl of a goat antibody against mice IgG which has been purified by affinity chromatography and is in the form of a 1:1500 dilution in PBS-Tween (0.1%) (Kirkegaard & Perry Laboratories) and is labelled with alkaline phosphatase are added to each well.

The incubation time is 1.5 hours at room temperature. The individual wells are then again washed (5×) with PBS-Tween (0.1%).

Then 150 μl of a substrate-containing solution (1 mg/ml p-nitrophenyl phosphate) are placed in each well. An incubation time of 2 hours in the dark is followed by the spectroscopic determination at 405 nm. Positive hybridoma cells which secrete a specific antibody give a strong positive signal at the selected wavelength.

Example 7: Expansion of the hybridoma cells in the mouse

To stimulate ascites production, female Balb/c mice (20 g–25 g) (Tierfarm Sisseln, CH) are pretreated with 0.3 ml of pristane oil (Aldrich Chemical) which is injected intraperitoneally. 1 to 3 weeks after the pristane administration the mice are given a second injection (0.2 ml of pristane oil, i.p.). At the same time as this 2nd injection the animals receive $2\times10^6$ hybridoma cells in 0.2 ml of PBS.

The ascites fluid resulting from this treatment is collected, centrifuged at 800 g and stored at a temperature of $-20°$ C. After thawing, the ascites fluid is centrifuged at 30,000 g for 1 hour. The top layer, which contains predominantly lipids, is removed. The protein concentration is then determined and adjusted to a value of 10 mg/ml by adding PBS.

The immunoglobulin G fraction (IgG) is precipitated by dropwise addition of 0.9 parts by volume of a saturated ammonium sulfate solution at $0°$ C. After 1 hour, the IgG fraction is pelleted by centrifugation at 22,000 g for 1 hour. The pellet is then dissolved in 20 mM tris-HCl buffer, pH 7.9, which contains 50 mM NaCl, and dialysed against the same buffer at $4°$ C. overnight.

The subsequent working up of the IgG fraction takes place by anion exchange chromatography on a DE-52 diethylaminoethylcellulose (Whatman) column. The sample is diluted 1:2 (v/v) with 20 mM tris-HCl, pH 7.9, until a final concentration of 25 mM NaCl is reached and 10 mg of protein/ml of gel are loaded on the column. Elution is achieved by increasing the NaCl concentration from 25 mM to 200 mM (linear gradient). Monoclonal antibodies are generally eluted in the region of 80 mM NaCl.

The fractions are dialysed against PBS at a temperature of $4°$ C. overnight and stored at $-70°$ C. The purity is determined by means of sodium dodecyl sulfate polyacrylamide gel electrophoresis (SDS-PAGE) and by isoelectric focusing.

The purity in the present case is >90%.

Example 8: Metolachlor detection 8.1: Indirect ELISA (assay A)

Metolachlor is detected by means of a two-stage competitive ELISA test using an enzyme-labelled second antibody.

BSA-conjugated hapten in a 50 mM sodium carbonate buffer (pH 9.6) (200 ng of BSA-conjugated hapten/100 μl of sodium carbonate buffer) is initially adsorbed onto microtitre plates (for example Dynatech, type M 129A) and incubated at a temperature of $4°$ C. overnight. It has emerged that the sensitivity of the assay can be increased almost 5-fold by reducing the conjugate[BSA/hapten] concentration from 200 ng/100 μl of sodium carbonate buffer to 50 ng/100 μl of sodium carbonate buffer because the coating is improved.

The plates are then washed 5× with PBS buffer which is supplemented with 0.1% (v/v) polysorbate 20 (Tween 20) (PBS-Tween).

The remaining free binding sites on the solid support material are then blocked by adding BSA in the form of a 1% solution. After incubation at $22°$ C. for two hours the plates are again washed with PBS-Tween (0.1%).

50 μl of the previously purified monoclonal antibodies (0.2 μg/ml) or else of the supernatant of the cell clones (in a dilution of 1:15) are incubated a) with 950 μl of a standard solution which contains an increasing content of metolachlor or metolachlor analogue, b) with metolachlor-containing water samples or c) metolachlor-containing soil extracts. (PBS-Tween is used for all dilutions).

After an incubation time of 1 hour at room temperature ($22°$ C.), 200 μl of the antigen/antibody mixture are added to each well of the microtitre plate, and the entire mixture is incubated for a further hour. The wells are then washed 5× with PBS-Tween (0.1%) and charged with 100 μl/well of goat anti-mouse IgG antibody which is conjugated to alkaline phosphatase (dilution 1:1500) and incubated for a period of 1.5 hours.

After renewed washing, 150 μl/well of the substrate p-nitrophenyl phosphate which is dissolved in 1 mg/ml diethanolamine buffer (1 mM, pH 9.8, supplemented with 0.5 mM $MgCl_2\times6H_2O$) are added to the wells.

After an incubation time of 2 hours at a temperature of $22°$ C. it is possible to observe a colour change which is proportional to the amount of antibody which has reacted with the antigen bound to the solid phase. The intensity of the colour reaction which has occurred is determined at a wavelength of 405 nm. The dilutions of the individual samples are chosen so that absorptions in a range between 0.3 and 0.5 are obtained without addition of an inhibitor (Bo). Values of $R\leq0.005$ are found for the controls (without antibody and with undetectable amounts of antigen). All the samples are determined in triplicate.

8.2: Direct ELISA (assay B)

Microtitre plates [Dynatech M 129A] are coated with monoclonal antibodies [for example MAb 4082-25-4; 75 ng/100 μl of 50 mM sodium carbonate buffer, pH 9.6] and incubated at a temperature of $4°$ C. overnight. The plates are then washed 5 times with 0.1% (v/v) PBS-Tween and subsequently incubated with PBS supplemented with 1% (w/v) BSA for 2 hours in order to block the binding sites which are still free. After renewed washing, 150 μl of a standard solution are added to each of the wells of the microtitre plates which contain increasing amounts of metolachlor in 0.1% (v/v) PBS-Tween. This is followed by incubation at a temperature of $22°$ C. for 1 hour. Then 50 μl of the hapten-enzyme [alkaline phosphatase] conjugate [2 μg/ml] are added to each well and the incubation is continued for a further hour. After renewed washing, 150 μl of the p-nitrophenyl phosphate substrate in a concentration of 1 mg/ml in diethanolamine buffer [1 mM, pH 9.8, supplemented with 0.5 mM $MgCl_2\bullet6H_2O$] are added to each well.

After incubation at 22° C. in the dark for 2 hours, the absorption of 405 nm is determined.

8.3: Determination of the metolachor content

For the determination of the amount of metolachlor contained in a sample, initially a calibration plot is constructed (FIG. 1), where B/Bo×100 is plotted against the concentration of inhibitor. (Bo represents the absorbance measured without addition of a metolachlor inhibitor to the antibody, and B means the absorbance measured with various concentrations of metolachlor inhibitor). The $I_{50}$ value indicates that concentration of the antigen at which the antibody binding to the solid phase is inhibited by 50%. The $I_{50}$ value is calculated using an ENZFITTER (Leatherbarrow, Elsevier-Biosoft) plot calculation program specifically adapted to the present circumstances and based on a logistic plot embracing 4 parameters (Raab GM, 1983). The quantitative determination of metolachlor in samples of soil or water within the scope of the ELISA is also carried out using the ENZFITTER program, with the fitting of the plot being based on standards included on each microtitre plate.

Example 9: Analysis of soil samples

Aliquots (2 g) of standardised soil samples of various origins are extracted with 20 ml of a methanol/water [80/20 (v/v)] mixture in an extractor for 4 hours. The soil extracts are normally diluted in a ratio of 1:40 in PBS-Tween (0.1%) for the competitive ELISA in order to prevent the possibility of denaturation of the monoclonal antibodies by the methanol. The diluted soil samples (950 μl) are then either mixed with the specific anti-metolachlor antibody [MAb 4082-85-4] (50 μl) and then incubated with the carrier-bound hapten [indirect ELISA] or else reacted directly with the carrier-bound anti-metolachlor antibodies and then incubated with enzyme-labelled antigen [direct ELISA], in the manner described previously.

Example 10: Analysis of water samples

For the competitive ELISA, 100 μl of a 10-fold concentrated PBS-Tween buffer are added to 850 μl of a water sample. The metolachlor determination can then be carried out in analogy to the procedure described previously [compare Example 9].

II. RESULTS a) Preparation of monoclonal antibodies

In total, 24 cell fusions between myeloma cells and spleen cells which have previously been isolated from a BALB/c mouse immunised with a KLH-metolachlor are carried out. The fusion efficiency is about 90%. 7 of the cell colonies obtainable in this way produce monoclonal antibodies which show a very strong reaction in the ELISA test. These are cloned using the limiting dilution method (compare section 5).

It was possible in this way to obtain 7 monoclonal antibodies, one of which [MAb 4082-25-4; (IgGl subclass)] shows a very high affinity for metolachlor, while the affinity of the other 6 monoclonal antibodies remains confined to the metolachlor derivative. This antibody was used to develop two competitive immunoassays. One of these assays is based on the use of microtitre plates which are coated with BSA-hapten conjugate and of enzyme-labelled goat/anti-mouse antibodies [indirect ELISA]. The second assay uses hapten-enzyme conjugates and antibody-coated microtitre plates [direct ELISA].

Both assays are able to detect metolachlor in the ppb range. The direct ELISA is slightly less sensitive than the indirect, but is compensated by being much quicker. The $I_{50}$ values are 1.0 ng/ml for the direct and 0.6 ng/ml for the indirect ELISA. The detection range for metolachlor in buffer is between 0.1 ng/ml and 10 ng/ml, where the minimum detection limit is defined as that concentration required to achieve a percentage increase in the bound antibody which corresponds to twice the standard deviation of the blank. The coefficient of variation for repeated determinations in the 1 ppb range is 11% (20 determinations).

The cross-reactivity of MAb 4082-25-4 can be determined by means of an indirect competitive ELISA. As Table 1 shows, there is found to be a weak cross-reactivity of 1.4% with the structurally very closely related hydroxyl metabolite [compound A] of metolachlor. The other metabolites show no cross-reactivities [<0.1%]. The monoclonal antibody does not bind to other chloroacetanilide herbicides and related compounds such as, for example, alachlor, furalaxyl and matalaxyl [<0.1%].

Deposition

The hybridoma cell lines [4082-25-4] prepared and used within the scope of the present invention were deposited at the European Collection of Animal Cell Cultures (ECACC) in Salisbury, UK, which is a recognised International Depository, in accordance with the requirements of the Budapest Treaty on the international recognition of the deposite of microorganisms for the purposes of patent procedure, under deposit number ECACC 9002 1701. A certificate of viability of the deposited samples is being prepared by the said international depository.

III MEDIA AND BUFFERS (A) RPMI 1640 medium

RPMI 1640 (Seromed) with the following additions:

Calf serum 15%

L-Glutamine 4 mM

Gentamicin 0.01%

Sodium pyruvate 1 mM

2-Mercaptoethanol 50 μM

Insulin 5 μM

Transferrin 5 μM

Selenium (ITS) 5 μM (B) HAT medium 1 liter of RPMI 1640 medium with 20 ml addition of HAT conc. (50×) from Boehringer, which has the following composition:

Hypoxanthine 680 5.0 mg/l

Aminopterin 8.8 mg/l

Thymidine 193.8 mg/l (C) HT medium 1 liter of RPMI 1640 medium with 20 ml addition of HT conc. (50×) from Boehringer, which has the following composition:

Hypoxanthine 680 5.0 mg/l

Thymidine 193.8 mg/l (D) BSS buffer [Earle's saline without Ca and Mg, pH 7.4]

KCl 7.3 mM

NaCl 116.0 mM

NaHCO$_3$ 26.0 mM

NaH$_2$PO$_4$.2H$_2$O 1.0 mM

Glucose 5.5 mM

Phenol red 48.0 μM

1% addition (v/v) of a penicillin/streptomycin solution (Seromed) [10,000 U of penicillin, 10 mg/ml streptomycin]

(E) Sodium carbonate buffer [pH 9.6]

Na$_2$CO$_3$ 477.0 mg

NaHCO$_3$ 879.0 mg

NaN$_3$ 1.8 mg ad 300 ml H$_2$O (F) PBS buffer [pH 7.0]

NaCl 8.5 g

Na$_2$HPO$_4$.2H$_2$O 1.28 g

NaH$_2$PO$_4$.2H$_2$O 0.436 ad 1000 ml H$_2$O (G) PBS-TWEEN-20 [0.1%]

1 ml Tween-20 (Serva)+1000 ml PBS (H) PBS-BSA [1%]

BSA 5.0 g

NaN$_3$ (0.5M) 3.0 ml ad 500 ml PBS (I) Substrate buffer [diethanolamine buffer, pH 9.8]

Diethanolamine 97.0 ml

NaN$_3$ (0.5M) 6.0 ml

MgCl$_2$·6H$_2$O 100.0 mg ad 1000 ml H$_2$O, adjust the pH to pH 9.8 with HCl conc. Preparation of the substrate: Immediately before use, one substrate tablet (=5 mg) of the p-nitrophenyl phosphate substrate (Sigma 104) is dissolved in 5 ml of substrate buffer.

TABLE 1

Cross-reactivity of the best known metolachlor analogues with MAb 4082-25-4 [the metolachlor analogues A to N are represented in Table 2 by means of their formula].

| Compound | I$_{50}$ [ng/ml]* | Cross-reactivity [%]# |
|---|---|---|
| Metolachlor | 0.6 | 100 |
| Alachlor | >1000 | <0.1 |
| A | 43 | 1.4 |
| B | >1000 | <0.1 |
| C | >1000 | <0.1 |
| D | >1000 | <0.1 |
| E | >1000 | <0.1 |
| F | >1000 | <0.1 |
| G | >1000 | <0.1 |
| H | >1000 | <0.1 |
| I | >1000 | <0.1 |
| J | >1000 | <0.1 |
| K | >1000 | <0.1 |
| L | >1000 | <0.1 |
| M | >1000 | <0.1 |
| N | >1000 | <0.1 |

*I$_{50}$ = Inhibitor concentration for 50% inhibition in the competitive ELISA.
Cross-reactivity = Metolachlor concentration for 50% inhibition /concentration of metolachlor analogue for 50% inhibition × 100.

TABLE 2

Table 2 shows the best known metolachlor analogues of the formula

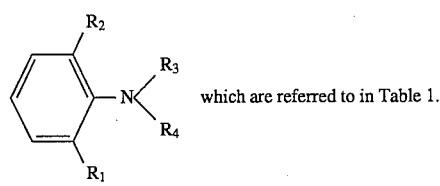

which are referred to in Table 1.

| Compound | R$_1$ | R$_2$ | R$_3$ | R$_4$ |
|---|---|---|---|---|
| Metolachlor | C$_2$H$_5$ | CH$_3$ | COCH$_2$Cl | CH(CH$_3$)CH$_2$OCH$_3$ |
| Alachlor | C$_2$H$_5$ | C$_2$H$_5$ | COCH$_2$Cl | CH$_2$OCH$_3$ |
| A | C$_2$H$_5$ | CH$_3$ | COCH$_2$OH | CH(CH$_3$)CH$_2$OCH$_3$ |
| B | C$_2$H$_5$ | CH$_3$ | H | CH(CH$_3$)CH$_2$OCH$_3$ |
| C | C$_2$H$_5$ | CH$_3$ | COCH$_2$Cl | H |
| D | C$_2$H$_5$ | CH$_3$ | COCH$_2$OH | H |
| E | C$_2$H$_5$ | CH$_3$ | H | CH(CH$_3$)CH$_2$OH |
| F | C$_2$H$_5$ | CH$_3$ | COCH$_2$OH | CH(CH$_3$)CH$_2$OH |
| G | CH$_3$ | CH$_3$ | COCH$_2$OCH$_3$ | CH(CH$_3$)COOH |

TABLE 2-continued

Table 2 shows the best known metolachlor analogues of the formula

| Compound | R$_1$ | R$_2$ | R$_3$ | R$_4$ |
|---|---|---|---|---|
| H | CH$_3$ | CH$_3$ | COCH$_2$OH | CH(CH$_3$)COOH |
| I | CH$_3$ | CH$_3$ | H | CH(CH$_3$)COOCH$_3$ |
| J | CH$_3$ | CH$_3$ | COCH$_2$OCH$_3$ | H |
| K | CH$_3$ | CH$_3$ | H | CH(CH$_3$)COOH |
| L | CH$_3$ | CH$_3$ | COCH$_2$OCH$_3$ | CH(CH$_3$)COOCH$_3$ |
| M | CH$_2$OH | CH$_3$ | COCH$_2$OCH$_3$ | CH(CH$_3$)COOCH$_3$ |
| N | CH$_3$ | CH$_3$ | CO-furan | CH(CH$_3$)COOCH$_3$ |

IV LITERATURE

Ercegovich CD et al, *J, Agric. Food Chem.*, 29: 559–563, 1981

Feng et al, *J. Agric. Food Chem.*, 38: 159–163, 1990

Fleeker J, *J. Assoc. Off. Anal. Chem.*, 70: 874–878, 1987

Hargrave HS and Merkle MG, *Weed Sci.*, 19: 1971

Kawamura H, Berzojsky JA, *J. Immunol.*, 136: 58, 1986

Kelley M et al, *J. Agric. Food Chem.*, 33: 962–965, 1985

Köhler G, Milstein, *Nature*, 256: 495–497, 1975

Kulkarni NP et al, *Cancer Res.*, 41: 2700–2706, 1981

Littlefield JW, *Science*, 145: 709, 1964

Newsome WH, *J. Agric. Food Chem.*, 33: 528–530, 1985

Raab GM, *Clin. Chem.*, 29: 1757–1761, 1983

Schlaeppi J-M et al, *J. Agric. Food Chem.*, 37: 1532–1538, 1989

Shulman M et al, *Nature*, 276: 269–270, 1978 van Rensburg E, *Analyst*, 110: 733., 1985

Wie SI, Hammock BD, *J. Agric. Food Chem.*, 30: 949–957, 1982

Patent literature

U.S. Pat. No. 4,530,786

We claim:

1. A hybridoma cell line which produces a monoclonal antibody which has the characteristic features of ECACC 9002 1701 including mutants and variants thereof.

2. A hybridoma cell line according to claim 1, which produces a monoclonal antibody which has a high specificity and affinity for metolachlor and which shows essentially no cross-reactivity with the structurally closely related alachlor.

3. A hybridoma cell line according to claim 1, which produces a monoclonal antibody which has a high specificity and affinity for metolachlor and which shows a cross-reactivity with the best known structurally related metolachlor analogues of <10%.

4. A hybridoma cell line according to claim 1, which produces a monoclonal antibody which has a high specificity and affinity for metolachlor and which shows a cross-reactivity with the best known structurally related metolachlor analogues of <2%.

5. A monoclonal antibody and derivatives thereof which is produced by a hybridoma cell line which has the characteristic features of ECACC 9002 1701.

6. A monoclonal antibody and derivatives thereof according to claim 5, characterized in that the cross-reactivity with the best known structurally related metolachlor analogues is <10%.

7. A monoclonal antibody and derivatives thereof according to claim 5, characterised in that the cross-reactivity with the best known structurally related metolachlor analogues is <2%.

8. A monoclonal antibody produced by a hybridoma cell line according to claim 1, and derivatives thereof derived by fragmentation, radioactive labelling, or conjugation.

9. Process for the preparation of a hybridoma cell line according to claim 1, comprising
   a) synthesising a suitable metolachlor derivative and conjugating the said derivative with a carrier molecule;
   b) immunising a donor animal with said conjugate;
   c) isolating an immunocompetent B cell from the immunised donor animal;
   d) fusing said immunocompetent B cell with a tumour cell line which is capable of continuous cell division;
   e) isolating the resulting fusion product, cultivating it in a suitable culture medium and subsequently cloning positive hybrid cells; and
   f) screening the cloned hybrid cells for the production of monoclonal antibodies, and selecting those which show the required properties;

wherein said metolachlor derivative is a compound of the formula (I)

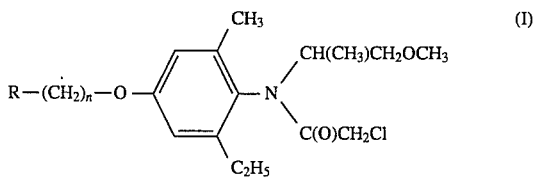

which has the 4 position with respect to the amino functionality of metolachlor an $R-(CH_2)_n-O-$ group in which R represents COOH, $NH_2$ or SH, and n represents an integer from 1 to 10.

10. Process according to claim 9, wherein macromolecular compounds which have reactive groups which are freely accessible for the coupling reaction with a suitable metolachlor derivative and are able to confer an immunogenic potency on said metolachlor are used as carrier molecule.

11. Process according to claim 10, wherein a lysine-rich protein with a molecular weight between 10,000 and 1,500,000 is used.

12. Process according to claim 10, wherein a protein selected from the group consisting of bovine serum albumin (BSA), keyhole limpet hemocyanin (KLH), human serum albumin (HSA), porcine thyroglobulin, B2 microglobulin, hemocyanin, immunoglobulins; toxins; polysaccharides; lipopolysaccharides; natural or synthetic polyadenylic and polyuridylic acids; polyalanyl and polylysine polypeptides; or cell membrane components is used.

13. Process according to claim 9, wherein the the metolachlor is directly conjugated to the carrier molecule.

14. Process according to claim 9, wherein the metolachlor is conjugated to the carrier molecule via a bridging element (spacer).

15. Process according to claim 14, wherein said bridging element has one or more reactive groups which are able to interact with the reactive groups of the carrier molecule.

16. Process according to claim 15, wherein said reactive groups are carboxyl, amino or SH groups.

17. Process according to claim 9, wherein the coupling reaction is carried out by the active ester method.

18. Process according to claim 9, wherein the donor animals are immunised by administration one or more times of carrier-bound metolachlor.

19. Process according to claim 18, wherein administration takes place in the form of an intravenous, intraperitoneal or subcutaneous injection or of a combination thereof.

20. Process according to claim 9, wherein tumour cell lines which themselves produce no monoclonal antibodies are used for the fusion of immunocompetent cells from the donor animal.

21. Process according to claim 20, wherein myeloma cell lines which have the characterising features of Sp2/0-Ag14 or X63-Ag8.653 are used.

22. Process according to claim 9, wherein the fusion medium used is a buffer solution which contains one of the fusion promoters customarily used for fusing cells, selected from the group consisting of Sendai viruses or other paramyxoviruses, calcium ions, surface-active lipids or polyethylene glycol.

23. Process according to claim 22, wherein said fusion promoters comprise polyethylene glycol with an average molecular weight of 600 to 6000.

24. Process according to claim 23, wherein the polyethylene glycol concentration in the fusion medium is 30%–60%.

25. Process according to claim 9, wherein the HAT selection medium is used for the selection of fused hybrid cells.

26. Process according to claim 9, wherein the hybrid cells are cultivated in the presence of isolated macrophages (feeder cells).

27. Process according to claim 9, wherein positive hybrid cell cultures producing monoclonal antibodies are singled out using the limiting dilution method and subsequently cloned in suitable cultivation media.

28. Process according to claim 9, wherein the hybridoma cell clones cloned according to claim 31 are investigated for the production of suitable monoclonal antibodies by means of an immunoassay.

29. Process according to claim 28, wherein an enzyme-coupled immunoassay or a radioimmunoassay is used.

30. Process for the preparation of monoclonal antibodies, wherein a hybridoma cell line prepared according to claim 9 is cultivated in vivo or in vitro using known methods, and the produced monoclonal antibodies are isolated.

31. Process according to claim 30, wherein an in vitro cultivation is carried out in suitable cultivation media.

32. Process according to claim 31, wherein standardised culture media selected from the group consisting of Dulbecco's modified Eagle medium (DMEM) or RPMI 1640, which can, where appropriate, be supplemented by addition of mammalian sera, by growth-promoting additives or by trace elements, are used.

33. Process according to claim 30, wherein said monoclonal antibodies are produced in vivo by expansion of a hybridoma cell line prepared according to claims 12 in a donor animal.

34. Method for the immunological detection of metolachlor in a sample, wherein a monoclonal antibody of claim 5 is used in one of the known immunoassays to bind to hapten present in the sample.

35. Method for the immunological detection of metolachlor according to claim 34, wherein a monoclonal antibody which is produced by a hybridoma cell line which has the characterising features of ECACC 9002 1701 or by clones or subclones thereof is used in one of the known immunoassays.

36. Method according to claim 34, wherein a competitive immunoassay is used.

37. Method according to claim 34, wherein said immunoassay is a radioimmunoassay (RIA), an enzyme-coupled assay (ELISA) or a chemiluminescence assay.

38. Method according to claim 37, wherein said enzyme-coupled assay is an indirect ELISA.

39. Method according to claim 37, wherein said enzyme-coupled assay is a direct ELISA.

40. Composition for the immunological detection of metolachlor in the form of a test kit which is ready to use, wherein said test kit contains, besides the customarily used support materials, reagents and other additives, at least one monoclonal antibody according to claim 5 as reagent.

41. Composition for the immunological detection of metolachlor in the form of a test kit which is ready to use, according to claim 40, wherein said test kit contains, besides the customarily used support materials, reagents and other additives, at least one monoclonal antibody which is produced by a hybridoma cell line which has the characteristic features of ECACC 9002 1701 or by clones or subclones thereof.

42. A hybridoma cell line according to claim 1, which hybridoma cell line produces a monoclonal antibody which has a high specificity and affininty for metolachlor and which shows essentially no cross-reactivity with the best known structurally related metolachlor analogues listed in table 2 of the specification.

43. A monoclonal antibody and derivatives thereof according to claim 5, which have a high specificity and affinity for metolachlor and which show essentially no cross-reactivity with the best known structurally related metolachlor analogues listed in table 2 of the specification.

* * * * *